United States Patent
Ramanand et al.

(10) Patent No.: US 11,786,618 B2
(45) Date of Patent: Oct. 17, 2023

(54) MULTIPURPOSE ULTRAVIOLET FLOOR CURING DEVICES

(71) Applicant: Anram Holdings, Mississauga (CA)

(72) Inventors: Prakash Valentino Ramanand, Burlington (CA); Manjinder Singh Dhillon, Milton (CA)

(73) Assignee: Anram Holdings, Oakville (CA)

( * ) Notice: Subject to any disclaimer, the term of this patent is extended or adjusted under 35 U.S.C. 154(b) by 129 days.

(21) Appl. No.: 17/330,734

(22) Filed: May 26, 2021

(65) Prior Publication Data

US 2021/0290797 A1 Sep. 23, 2021

Related U.S. Application Data

(63) Continuation of application No. 16/288,792, filed on Feb. 28, 2019, now Pat. No. 11,058,784.

(Continued)

(51) Int. Cl.
*A61L 2/10* (2006.01)
*F26B 3/28* (2006.01)
(Continued)

(52) U.S. Cl.
CPC ........ *A61L 2/10* (2013.01); *A61L 2/24* (2013.01); *F26B 3/28* (2013.01); *F26B 9/003* (2013.01);
(Continued)

(58) Field of Classification Search
CPC .......... A61L 2/10; A61L 2/24; A61L 2202/14; A61L 2202/16; A61L 2202/20; B29C 2035/0827
See application file for complete search history.

(56) References Cited

U.S. PATENT DOCUMENTS

| 2,273,449 A | 2/1942 | Plishker |
| 4,583,798 A | 4/1986 | Blazowich |

(Continued)

FOREIGN PATENT DOCUMENTS

| CA | 2644766 A1 | 5/2010 |
| CA | 2982445 A1 | 10/2016 |
| JP | 2001121552 A1 | 5/2001 |

OTHER PUBLICATIONS

WIPO: International Search Report relating to PCT application No. PCT/CA2019/050238, dated Jun. 10, 2019.

(Continued)

*Primary Examiner* — Timothy C Cleveland
(74) *Attorney, Agent, or Firm* — Rowand LLP

(57) ABSTRACT

Embodiments of the present disclosure disclose a multipurpose ultraviolet (UV) floor curing device. The device includes a mobile carriage, a UV panel, and a control device. The mobile carriage is configured to move on a floor applied with a photocurable coating. The UV panel is coupled to the mobile carriage and removably secures a plurality of radiation units configured to emit UV light of a predetermined intensity capable of curing the photocurable coating. The UV panel is configured to transition between a floor configuration and a non-floor configuration. The control device configured to drive the UV panel for the plurality of radiation units to project the UV light towards the ground substantially underneath the UV panel in the floor configuration and towards elevated surfaces proximate to the ground in the non-floor configuration.

20 Claims, 12 Drawing Sheets

Related U.S. Application Data

(60) Provisional application No. 62/636,443, filed on Feb. 28, 2018.

(51) Int. Cl.
*F26B 9/00* (2006.01)
*A61L 2/24* (2006.01)
*B29C 35/08* (2006.01)

(52) U.S. Cl.
CPC ....... *A61L 2202/14* (2013.01); *A61L 2202/16* (2013.01); *A61L 2202/20* (2013.01); *B29C 2035/0827* (2013.01)

(56) References Cited

U.S. PATENT DOCUMENTS

| | | |
|---|---|---|
| 6,207,118 B1 | 3/2001 | Gaven et al. |
| 6,538,258 B1 | 3/2003 | Rau et al. |
| 7,581,283 B2 | 9/2009 | Yoo et al. |
| 8,481,985 B2 | 9/2013 | Neister |
| 8,779,391 B2 | 7/2014 | Flaherty et al. |
| 9,165,756 B2 | 10/2015 | Stribich et al. |
| 2010/0242298 A1 | 9/2010 | Tweedy et al. |
| 2013/0340273 A1 | 12/2013 | Mackinnon et al. |
| 2014/0246602 A1 | 9/2014 | Wilson et al. |
| 2017/0112954 A1* | 4/2017 | Dayton .................... A61L 9/20 |

OTHER PUBLICATIONS

CIPO, Examiner's Report relating to CA Application No. 3,089,235 dated Oct. 14, 2021.

* cited by examiner

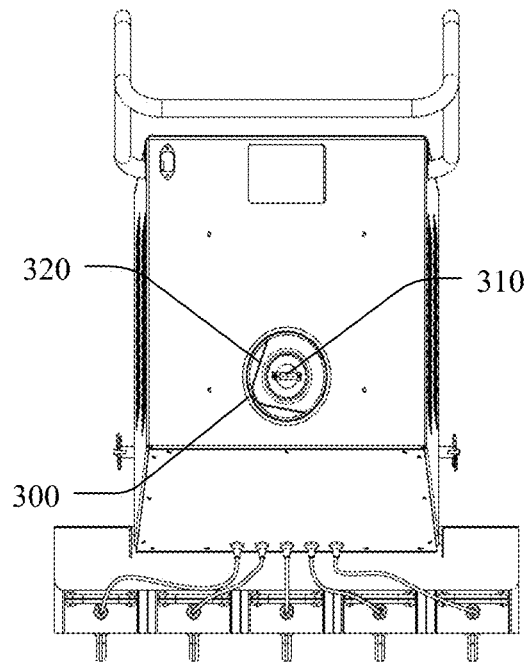
FIG. 12
FIG. 13
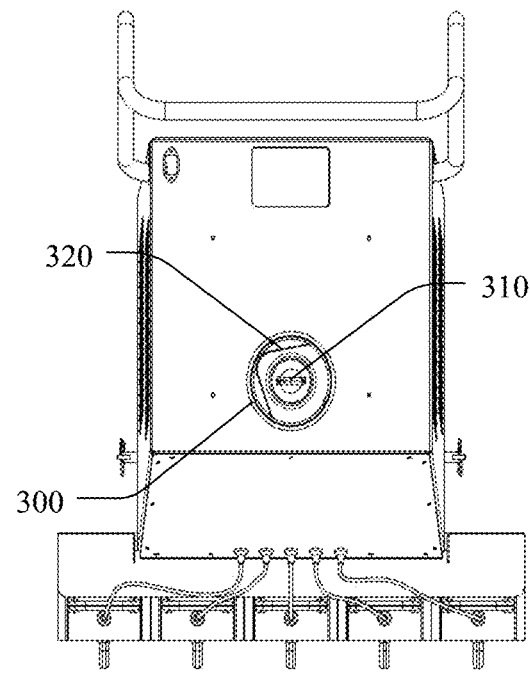

MULTIPURPOSE ULTRAVIOLET FLOOR CURING DEVICES

CROSS-REFERENCE TO RELATED APPLICATIONS

The present patent application incorporates the subject matter of the following patent applications, by reference and in their entirety: U.S. Provisional Patent Application Ser. No. 62/636,443, filed Feb. 28, 2018, and U.S. patent application Ser. No. 16/288,792, filed Feb. 28, 2019, and titled "MULTIPURPOSE ULTRAVIOLET FLOOR CURING DEVICES," in which the inventors herein were listed as co-inventors.

TECHNICAL FIELD

The subject matter described herein generally relates to ultraviolet (UV) devices for curing of radiation-curable surface coatings and particularly relates to multipurpose UV floor curing devices.

BACKGROUND

Over the years, ultraviolet (UV) light has found use in several applications ranging from sterilization to polymerization. In the floor preparation industry, UV light is employed to cure photosensitive coatings applied on the floor and surfaces proximate thereto for improving their stain resistance and durability. A wide variety of radiation-curable compositions or formulations are available in the market that can be used as such coatings. These compositions typically include photoinitiators, resins, and various additives for manipulating desired properties of such resins for intended applications or effect. During a UV curing process, the UV light is absorbed by the photoinitiators to polymerize or crosslink the resins and bind them to the floor. This process of UV curing is uber-effective in achieving a smooth and abrasion resistant floor surface with no toxic odor and allows for using the floor within minutes of treatment.

Modern UV floor curing devices typically include one or more UV lamps projecting high-intensity UV light on to the floor for curing the coatings applied thereon. The UV lamps are usually positioned proximate to the floor and directly face the floor to speed up the curing process by maximizing floor exposure to the high-intensity UV light. However, such positioning of the UV lamps fails to cure or disinfect surfaces (e.g., chair rails, wall trims, cornice, etc.) or objects (e.g., door knobs, bathroom sinks, etc.) that are located at a significant height from the floor and those within constrict spaces (e.g., walk-in closets, cabinets, etc.). As a result, such surfaces or objects are often cured or disinfected by employing a separate high-voltage UV unit that is bulky, difficult to maneuver, and adds to the cost of equipment, and maintenance thereof. Additionally, the state-of-the-art UV floor curing solutions are incapable of facilitating large area or room disinfection.

SUMMARY

Embodiments of the present disclosure describe a multipurpose ultraviolet (UV) floor curing device. One embodiment of the multipurpose UV floor curing device includes a mobile carriage, a UV panel, and a control device. The mobile carriage may be configured to move on a floor applied with a photocurable coating. The UV panel may be coupled to the mobile carriage and removably secure multiple radiation units configured to emit UV light of a predetermined intensity capable of curing the photocurable coating. The UV panel may be configured to transition between a floor configuration and a non-floor configuration. The control device may be configured to drive the UV panel for the plurality of radiation units to project the UV light towards the ground substantially underneath the UV panel in the floor configuration and towards elevated surfaces proximate to the ground in the non-floor configuration.

One aspect of the present disclosure is to provide an integrated device for ultraviolet-based curing and an area or room disinfection.

Another aspect of the present disclosure is to cure and disinfect the floor including surfaces proximate thereto, surfaces at a significant height from the floor, and surfaces within objects such as cabinets using the same UV source.

Yet another aspect of the present disclosure is to cure and disinfect the ceiling and surfaces proximate thereto.

Still another aspect of the present disclosure to provide a multipurpose ultraviolet device that is capable of disinfecting or curing radiation-curable coatings on spatially apart surfaces such as the floor, walls, and the ceiling in a room simultaneously.

Another aspect of the present disclosure is to provide an ultraviolet device capable of adjusting an intensity of projected UV light or that received by a target surface based on different orientations of the device or components thereof during use.

The above summary of exemplary embodiments is not intended to describe each disclosed embodiment or every implementation of the present disclosure. Other and further aspects and features of the disclosure will be evident from reading the following detailed description of the embodiments, which are intended to illustrate, not limit, the present disclosure.

BRIEF DESCRIPTION OF THE DRAWINGS

The illustrated embodiments of the subject matter will be best understood by reference to the drawings, wherein like parts are designated by like numerals throughout. The following description is intended only by way of example, and simply illustrates certain selected embodiments of devices, systems, and processes that are consistent with the subject matter as claimed herein.

FIG. 12 is a top elevation view of the MUFC device of FIG. 11 illustrating an exemplary first position of the rotatable reflector, according to an embodiment of the present disclosure.

FIG. 13 is a top elevation view of the MUFC device of FIG. 11 illustrating an exemplary second position of the rotatable reflector, according to an embodiment of the present disclosure.

DETAILED DESCRIPTION

Figure 1:
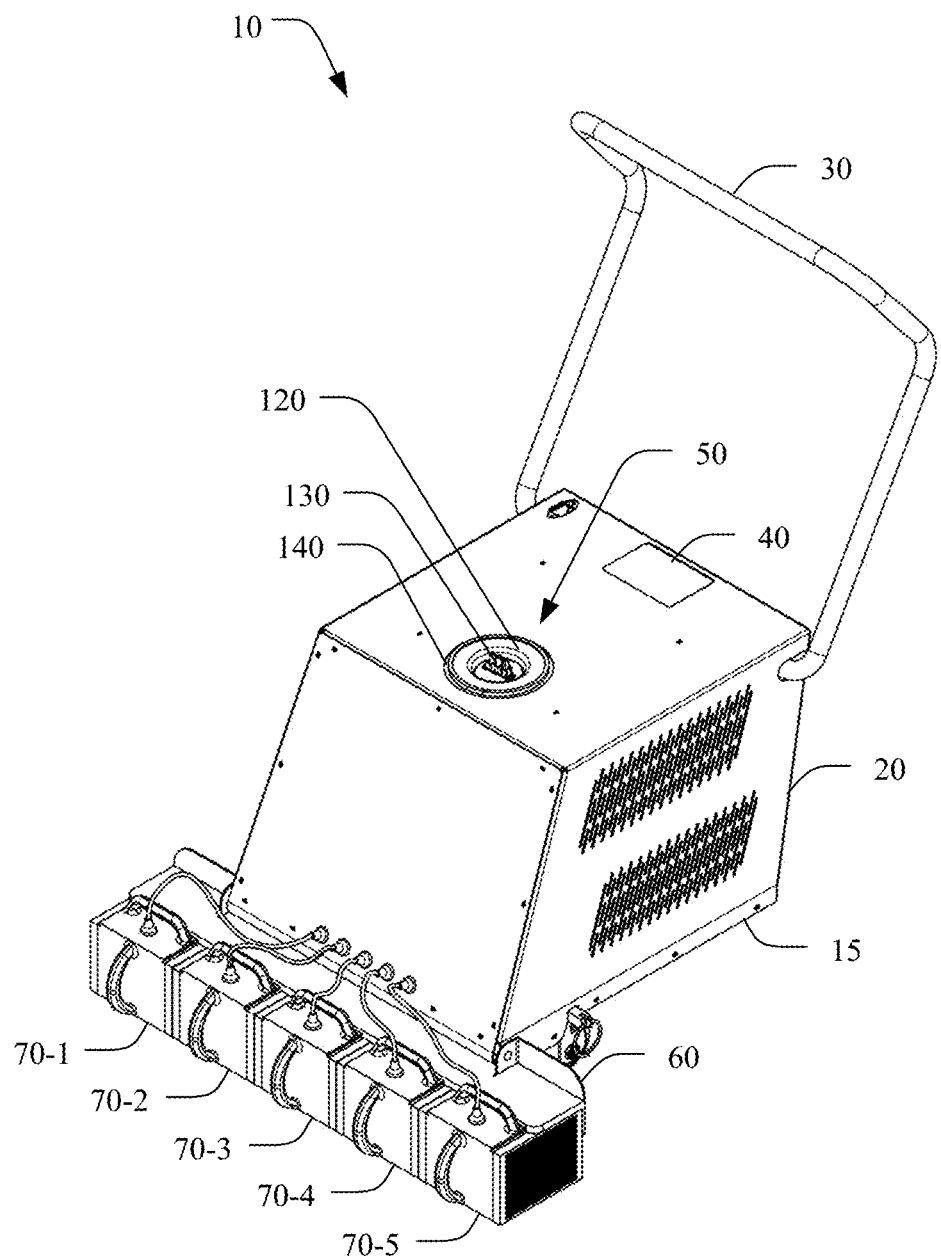
FIG. 1 is a right-side isometric view of an exemplary multipurpose ultraviolet (UV) floor curing device in a floor configuration, according to an embodiment of the present disclosure.

The following detailed description is provided with reference to the figures. Exemplary embodiments are described to illustrate the disclosure, not to limit its scope, which is defined by the claims. Those of ordinary skill in the art will recognize number of equivalent variations in the description that follows without departing from the scope and spirit of the disclosure.

Non-Limiting Definitions

Definitions of one or more terms that will be used in this disclosure are described below without limitations. For a person skilled in the art, it is understood that the definitions are provided just for the sake of clarity and are intended to include more examples than just provided below.

"Disinfection" is used in the present disclosure in the context of its broadest definition. The disinfection may refer to any process of inactivating or killing pathogens on a target surface using UV light alone or in combination with a variety of disinfectants known in the art, related art, or developed later including, but not limited to, chemical agents (e.g., alcohols, aldehydes, oxidizing agents, naturally occurring or modified compounds, etc.), physical agents (e.g., heat, pressure, vibration, sound, radiation, plasma, electricity, etc.), and biological agents (e.g., living organisms, plants or plant products, organic residues, etc.).

"Curing" is used in the present disclosure in the context of its broadest definition. The curing may refer to any process in which a radiation of a predetermined wavelength, frequency, intensity, or dose initiates a photochemical reaction in a radiation-curable formulation alone or in combination with a variety of agents such as those mentioned above.

"Area UV disinfection device" (also referred to as room UV disinfection device) is used in the present disclosure in the context of its broadest definition. The area UV disinfection device may refer to any device configured to emit or facilitate emission of UV pulses having predetermined characteristics suitable to disinfect a surface in a short period (e.g., approximately 10 minutes or less) from a relatively long distance (e.g., greater than approximately 1 meter from the surface). Examples of these characteristics may include, but are not limited to, intensity, frequency, power, wavelength, and dose.

Exemplary Embodiments

The present disclosure is described below in detail with reference to the drawings, which are provided as illustrative examples to enable those skilled in the art to practice the disclosure. Moreover, where certain elements of the present disclosure can be partially or fully implemented using known components, only those portions of such known components that are necessary for an understanding of the present invention will be described, and detailed descriptions of other portions of such known components will be omitted. In the present specification, an embodiment showing a singular component should not be considered limiting; rather, it is intended to encompass other embodiments including a plurality of the same component, and vice-versa, unless explicitly stated otherwise herein.

FIG. 1 is a right-side isometric view of an exemplary multipurpose ultraviolet floor curing (MUFC) device 10 in a floor configuration, according to an embodiment of the present disclosure. Embodiments are disclosed in the context of curing radiation-curable formulations (hereinafter interchangeably referred to as radiation-curable coatings, photocurable coatings, or photocurable formulations) including, but not limited to, those based on acrylated resins (e.g., epoxies, urethanes, polyesters, acrylics, or other specialty resins), cycloaliphatic epoxies, cationic epoxy, epoxy silane, and unsaturated polyester for surface protection, durability, and longevity. However, in general, the embodiments may be implemented to cure or disinfect any surface such as wood, metal, plastic, fiberglass, cement, stone, and ceramic, or the radiation-curable coatings on such surfaces in a wide variety of indoor and outdoor environments including, but not limited to, hospitals, cruise ships, homes, schools, factories, restaurants, stadiums, locker rooms, and gyms. These radiation-curable coatings or any of their constituents and reactants may be formulated in one or more forms such as solid, semi-solid, liquid, gas, and plasma, or any combinations thereof.

The MUFC device 10 may represent a wide variety of devices configured to emit or facilitate emission of the UV light at a high intensity towards surfaces proximate to the ground (e.g., floor surface, baseboards, etc.) as well as those at a significant height from the ground (e.g., walls, roofs, ceilings, objects such as drawers, storage cabinets, door knobs, and bathroom sinks, etc.), where the intensity may be adapted to induce an intended effect (e.g., curing, disinfection, sintering, etc.) within approximately sixty seconds or less from a relatively short distance (e.g., less than approximately one foot from such surfaces). The MUFC device 10 may be implemented as a standalone and dedicated device including hardware and installed software, where the hardware is closely matched to the requirements or functionality of the software. In some embodiments, the MUFC device 10 may enhance or increase the functionality or capacity of a network to which it may be connected.

The MUFC device 10 may also include software, firmware, or other resources that support remote administration, operation, diagnostics, repair, and/or maintenance thereof. Further, the MUFC device 10 may be implemented in communication with any of a variety of computing devices such as a desktop PC, a personal digital assistant (PDA), a server, a mainframe computer, a mobile computing device (e.g., mobile phones, laptops, etc.), an internet appliance (e.g., a DSL modem, a wireless access point, a router, a base station, a gateway, etc.), and so on. In some instances, the MUFC device 10 may operate, or cease to operate, in response to a wearable device including, but not limited to, a fashion accessory (e.g., a wrist band, a ring, etc.), a utility device (e.g., hand-held baton, a pen, an umbrella, a watch, etc.), a body clothing, or any combination thereof, present within a predetermined proximity of, or remotely connected to, the MUFC device 10.

The MUFC device 10 either independently or in communication with a network device may have video, voice, or data communication capabilities (e.g., unified communication capabilities) by being coupled to or including, various imaging devices (e.g., cameras, printers, scanners, medical imaging systems, etc.), various audio devices (e.g., microphones, music, players, recorders, audio input devices, speakers, audio output devices, telephones, speaker telephones, etc.), various video devices (e.g., monitors, projectors, displays, televisions, video output devices, video input devices, camcorders, etc.), or any other type of hardware, in any combination thereof. In some instances, the MUFC device 10 may comprise or implement one or more real-time protocols and non-real-time protocols known in the art, related art, or developed later to facilitate data transfer to the networked device.

In one embodiment, the MUFC device 10 may include a mobile carriage 15, a cabinet 20, a handle 30, a display unit 40, a control system, a power connector 50, and a UV panel 60 including one or more radiation units 70-1, 70-2, 70-3, 70-4, 70-5 (collectively, radiation units 70). The mobile carriage 15 may provide a platform for supporting various components such as the cabinet 20 and the UV panel 60. The mobile carriage 15 may include floor mobility devices, which may assist to drive the mobile carriage 15 in space based on a friction, magnetic levitation, cryogenic levitation, or any other motion principle known in the art, related art, or developed later. For example (FIG. 2), the mobile carriage 15 may include omnidirectional wheels such as wheels 80-1, 80-2, 80-3 (collectively, wheels 80) for navigating the MUFC device 10 to a desired position within a designated space such as a room. The mobile carriage 15 may be manually maneuvered or operate autonomously for designated movements or operation within a defined space. Other embodiments may include the mobile carriage 15 being controlled remotely by any computing device (not shown) known in the art such as those mentioned above over the network. The mobile carriage 15 may be partially or fully enclosed in the cabinet 20.

The cabinet 20 may refer to any housing configured to cover the mobile carriage 15 and protect one or more components mounted thereon. In some instances, the cabinet 20 may improve the aesthetics of the MUFC device 10. The cabinet 20 may be made of any durable, fire-retardant or fire-resistant, and light-weight polymers known in the art, related art, or developed later including, but not limited to, polyphenylene sulfide, polyamide-imide, polypropylene, and aramid polyamide polymers. The cabinet 20 may include components or pockets that may be permanently connected, detachably coupled, or integrally formed thereto based on intended purposes. For example, the cabinet 20 may include one or more utility pods (not shown) attached externally or internally to the cabinet 20, allowing for convenient on-board carrying of various tools, supplies and implements such as radiation-curable formulation, spare or auxiliary components such as standalone a handheld radiation unit 210 (discussed below in further detail), etc. Structurally, such pods may be of any suitable shape and size depending on items intended to be mounted, stowed, or stored therein. Various other kinds, sizes, and shapes of utility pods may also be contemplated based an intended purpose or items to be held therein. Further, the utility pods may be made of any suitable material known in the art, related art, or developed later including those described above for the cabinet 20, such that the material has suitable rigidity, mechanical tolerance, and resistance to the UV light or various other types of decontamination and disinfection agents known in the art.

The cabinet 20 may include openings or slots to accommodate the handle 30 and the display unit 40 for providing access thereto. Both the handle 30 and the display unit 40 may be permanently connected, removably coupled, or formed integral to the mobile carriage 15. The handle 30 may refer to any structure capable of assisting an operator to maneuver the MUFC device 10 from one point in space to another. In one example, the handle 30 may have a U-shaped structure including elongated arms connected to each other via a bar. The handle 30 may be configured for being moved between a folded position (not shown) and an unfolded position. In the folded position, the handle 30 may pivot from one or more connection points for being substantially parallel to the mobile carriage 15 or the floor. In the unfolded position, the handle 30 may pivot about the horizontal axis into a plane, which may be substantially vertical or at a predetermined angle relative to the mobile carriage 15. In the unfolded position, the handle 30 or any portion thereof may be accessed by the operator for maneuvering the MUFC device 10. In some other embodiments, the handle 30 may include one or more control units (e.g., buttons, rotary dials, speakers, cameras, light emitting units such as bulbs, displays, interactive touchscreens, etc.) to assist in controlling an intended operation of the MUFC device 10 or providing an indication in response thereof. Examples of such indication may include, but not limited to, audio, visual, haptic, or any combination thereof.

Further, the display unit 40 may be physically located on the MUFC device 10, as illustrated, or connected remotely to the MUFC device 10 over the network. The display unit 40 may be in communication with a user interface (not shown) indicating information pertaining to the operation of MUFC device 10. Different types of user interfaces, including those, which are touch controlled, key-controlled, joystick-controlled, motion-controlled, voice-controlled, and so on may be employed. The user interface may be either integrated or separately combined with the display unit 40 or the MUFC device 10, which may also include a variety of known, related art, or later developed interface(s), including software interfaces (e.g., an application programming interface, a graphical user interface, etc.); hardware interfaces (e.g., cable connectors, a keyboard, a card reader, a barcode reader, a biometric scanner, an interactive display screen, a printer, temperature sensors, light sensors, disinfection/curing sensors, pathogen sensors, etc.); or both. Such interface (s) may facilitate communication between various devices or components such as the UV panel 60 and the radiation units 70 associated with the MUFC device 10. In some embodiments, the interface(s) may facilitate communication with other networked devices capable of interacting with the MUFC device 10 over the network.

The display unit 40 may be or include an interactive display screen allowing an operator to access, control, or dynamically define different functionalities (e.g., automatic spatial movement of the MUFC device 10, dynamic detection or identification of pathogens or radiation-curable coatings, etc.) of the MUFC device 10. In one example, the display unit 40 may display a login/logout section and a dashboard. The login/logout section may allow an operator to selectively gain access for using the MUFC device 10. Upon being logged-in, the display unit 40 may display the dashboard providing a list of functionalities, modes, parameters, avatars, etc. that the operator may select or modify for a desired operation of the MUFC device 10. Other embodiments may include the display unit 40 including or providing a variety of tangible indicators (e.g., light emitting diodes, vibrators, speakers, etc.) or virtual indicators displayable on the dashboard (e.g., numeric indicators, alphanumeric indicators, or non-alphanumeric indicators, such as different colors, different color luminance, different patterns, different textures, different graphical objects, etc.) known in the art, related art, or developed later to indicate different aspects of the MUFC device 10. Examples of these aspects may include, but not limited to, values of operational parameters such as frequency, wavelength, dose, power, and intensity; a selected mode in operation; operational states of different components; and operation or performance aspects of a networked or physically connected accessory.

Further, the MUFC device 10 may include the UV panel 60 outside the cabinet 20. The UV panel 60 may be permanently connected, removably coupled, or formed integral to the mobile carriage 15 or the cabinet 20. For example, the UV panel 60 may be coupled to the mobile carriage 15 via an electromechanical scheme of members and linkages which may be controlled by the control system. The UV panel 60 may be located towards a front of the mobile carriage 15. However, a person having ordinary skill in the art would understand that such UV panel 60 may be additionally or alternatively located at any other regions, e.g., at the bottom or at opposing sides, of the mobile carriage 15.

In one implementation, as illustrated (FIGS. 1-2), the UV panel 60 may include an L-shaped panel having a rectangular plate and a flange extending perpendicularly therefrom in a direction away from the mobile carriage 15. The plate may be rotatably secured to the mobile carriage 15. Further, the plate in combination with the flange may be configured to detachably secure the radiation units 70. For example, the plate or the flange, or both, may include slots (not shown) to receive the radiation units 70, which may be secured into the slots through a snap fit; however, other suitable connection mechanisms known in the art, related art, or developed later including magnets, Velcro® patches, a screw fit, and a luer-lock, may be contemplated based on materials from which the radiation units 70, the plate, and flange may be made.

In another implementation (not shown), the UV panel 60 may include a housing having any suitable cross-section based on designs of radiation units 70 to be mounted or secured therein. For example, the housing may be shaped as a cuboid having a substantially rectangular cross-section; however, other suitable cross-sectional shapes including, but not limited to, circular, elliptical, oval, polygon, and irregular may be contemplated. The housing may be open from a top side and an opposing bottom side, which may face the ground. The bottom side may include one or more flanges (not shown) extending inward from a lower rim of the housing. Each of such flanges may extend partially across the length of the housing to form a panel window surrounded by the flanges, which may provide a flat surface for receiving the radiation units 70. The panel window may extend along the length of the housing, which may receive the radiation units 70 from its top side. Upon being received, the radiation units 70 may rest on the one or more flanges. In some examples, each of the one or more flanges may include slots that assist to removably secure the radiation units 70; however, other securing mechanisms known in the art, related art, or developed later including those mentioned above may be employed depending on the materials from which the radiation units 70 and the housing are made.

The UV panel 60 may be made as an integrated unit or a modular unit created by assembling multiple pieces together. The UV panel 60 may be manufactured of any suitable size, shape, and material based on dimensions of each of the radiation units 70 being received, the heat generated by those radiation units 70, mechanisms to be implemented for cooling the radiation units 70, and a size of surface being projected with the UV light or intended projection surface area during operation. Examples of such material may include, but not limited to, those mentioned above for the cabinet 20, or any other suitable materials known in the art, related art, or developed later. Further, the UV panel 60 may include openings or channels to facilitate airflow therethrough to assist in cooling the radiation units 70. However, additional cooling mechanisms based on those including, but not limited to, a blower, a suction source, or any combination thereof may be implemented on the UV panel 60 or the radiation units 70.

Figure 2:
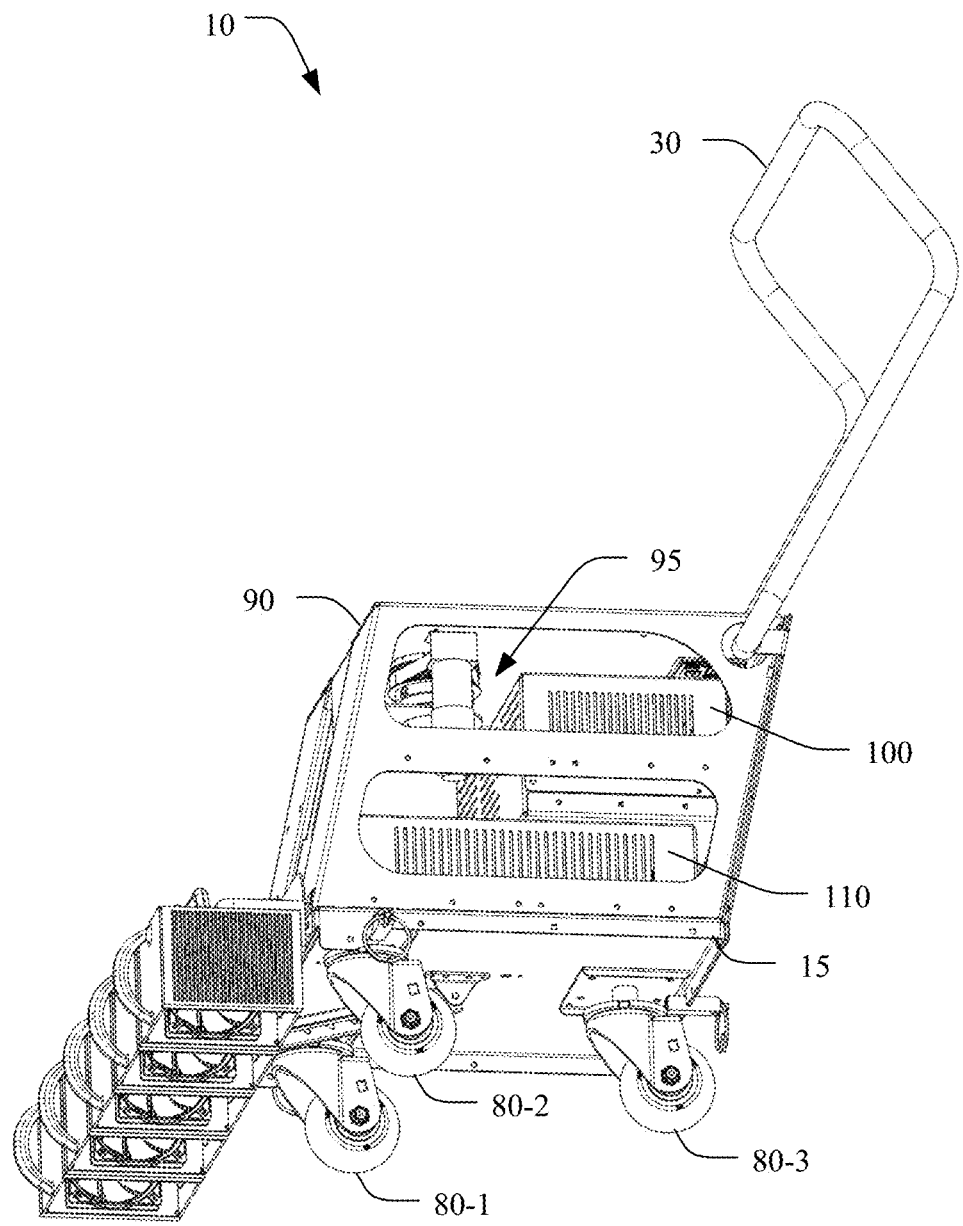
FIG. 2 is a right-side perspective view of the multipurpose UV curing (MUFC) device of FIG. 1 illustrating a bottom-side thereof without a cabinet, according to an embodiment of the present disclosure.

Further, as illustrated in FIG. 2, the mobile carriage 15 may further include a chassis 90 substantially covered by the cabinet 20. In one embodiment, the chassis 90 may support the control system having a control device 100 and a power supply unit 110. The power supply unit 110 may provide a high voltage power supply delivered from a set of one or more batteries placed on the mobile carriage 15, or an external electrical outlet via a power cord, which may be stored on a retractable reel disposed on the chassis 90 of the MUFC device 10. The control device 100 may be an electronic or an electromechanical device configured to control predefined or dynamically defined functions and movements of various components including, but not limited to, the mobile carriage 15 and the UV panel 60. In some embodiments, the control device 100 may include or be implemented by way of a single device (e.g., a computing device, processor or an electronic storage device) or a combination of multiple devices. The control device 100 may be implemented in hardware or a suitable combination of hardware and software.

In one embodiment, the control device 100 may be configured to operate the MUFC device 10 in predefined or dynamically defined modes such as a curing mode and a disinfection mode; however, one having ordinary skill in the art may contemplate to define and implement additional operational modes. In the curing mode, the control device 100 may be configured to drive the UV panel 60 in different orientations while the UV light is being emitted at a predetermined intensity and dose towards the floor and/or elevated surfaces located in a plane away from the floor, e.g., baseboards or trims running along the intersection of a wall and the floor. Further, the control device 100 may control the operation and movement of the radiation units 70 with respect to the UV panel 60. In some embodiments, the control device 100 may also release a desired radiation-curable formulation from the utility pods, or a storage tank contained therein, on to a target surface prior to projecting the UV light thereto. Other embodiments may include externally connected standalone radiation units 210, discussed below in detail, being operated to emit the UV light upon being triggered by the control device 100 for curing. Additionally, the control device 100 may allow an operator to remove or draw out the radiation units 70 from the UV panel 60 in the curing mode. In the disinfection mode, the control device 100 may lock the UV panel 60 to a predetermined orientation, e.g., facing the floor such that the UV radiation is projected towards the ground or a surface underneath the UV panel 60. In some embodiments, the functionalities of the MUFC device 10 activated in both the curing mode and the disinfection mode may be combined in a single operational mode.

The operator may select one of these modes either through an input device (not shown) located on the MUFC device 10 and in communication with the control device 100. Examples of the input device may include, but not limited to, a smartcard, a microphone, a stylus pen, the display unit 40, a keyboard, a camera, a switch, a rotary knob, a computing device, or any other input device known in the art, related, or developed later. Alternatively, the operator may select any of these modes remotely by a computing device such as those mentioned above in communication with the control device 100 over the network.

The control system may communicate with the power connector 50, which may be configured to power various standalone devices and components that are otherwise disconnected from the MUFC device 10. Examples of such standalone devices and components may include, but are not limited to, handheld UV units, mountable UV units, and accessories such as reflector panels, vacuum cleaners, blowers, and so on. The power connector 50 may include a body 120 having one or more electrical contacts 130 for engaging with an external accessory which may be referred to as an electrical accessory. The contacts 130 may have any of a variety of configurations known in the art, related art, or developed later. For example, the power connector 50 may be configured as a Type-L socket. On the other hand, the body 120 may be configured to rotate about a vertical axis based on a force induced by power cables (not shown) of the accessory upon being connected to the contacts 130. The body 120 may rotate freely or by a belt and motor arrangement 95 controlled by the control device 100, thereby facilitating omnidirectional maneuverability of the connected accessory and preventing the power cables, if any, of the accessory from tangling.

Structurally, the body 120 may also be configured to support any accessories mounted thereon. For example, the body 120 may be configured to include a recess 140 for receiving a portion of the mountable accessory. The recess 140 may have any of a variety of suitable shapes including, but not limited to, circular, rectangular, elliptical, and irregular depending on shapes of the accessories intended to be mounted therein. In one embodiment, the recess 140 may include rubber inner-walls for the accessory to snap fit therein. Another embodiment may include the recess 140 being part of a separate member (not shown) removably coupled to the body 120, where such separate member may be configured to rotate while the body 120 remains stationary. In some embodiments, the body 120 and the separate member may be configured to rotate independent of each other. In some other embodiments, the contacts 130 and the separate member may be powered at different voltage, current, or power levels by the control system. In some other embodiments, the power connector 50 may be configured to operate independent or in combination with the UV panel 60, or radiation units 70 contained therein, by the control device 100. For example, the control device 100 may disable or enable one or more standalone devices connected to the power connector 50 when the radiation units 70 are active based on a user input, and predefined or dynamically defined conditions such as an operating mode of the MUFC device 10.

Further, the UV panel 60 includes the radiation units 70, which may represent handheld units capable of emitting a desired pulsed or continuous radiation within a predetermined UV spectrum alone or in addition to other radiations within a predetermined wavelength range of the electromagnetic spectrum. For example, one or more of the radiation units 70 may be configured to emit the UV light within a wavelength ranging from 100 nm to 465 nm; however, other suitable wavelength ranges may be contemplated depending on the radiation-curable coatings applied to the floor or any other surfaces for being cured or disinfected. The control device 100 may adjust the intensity and dose of the UV light per unit area emitted generated by the radiation units 70 to speed up the curing process based on the radiation-curable formulation to be cured.

Figure 3:
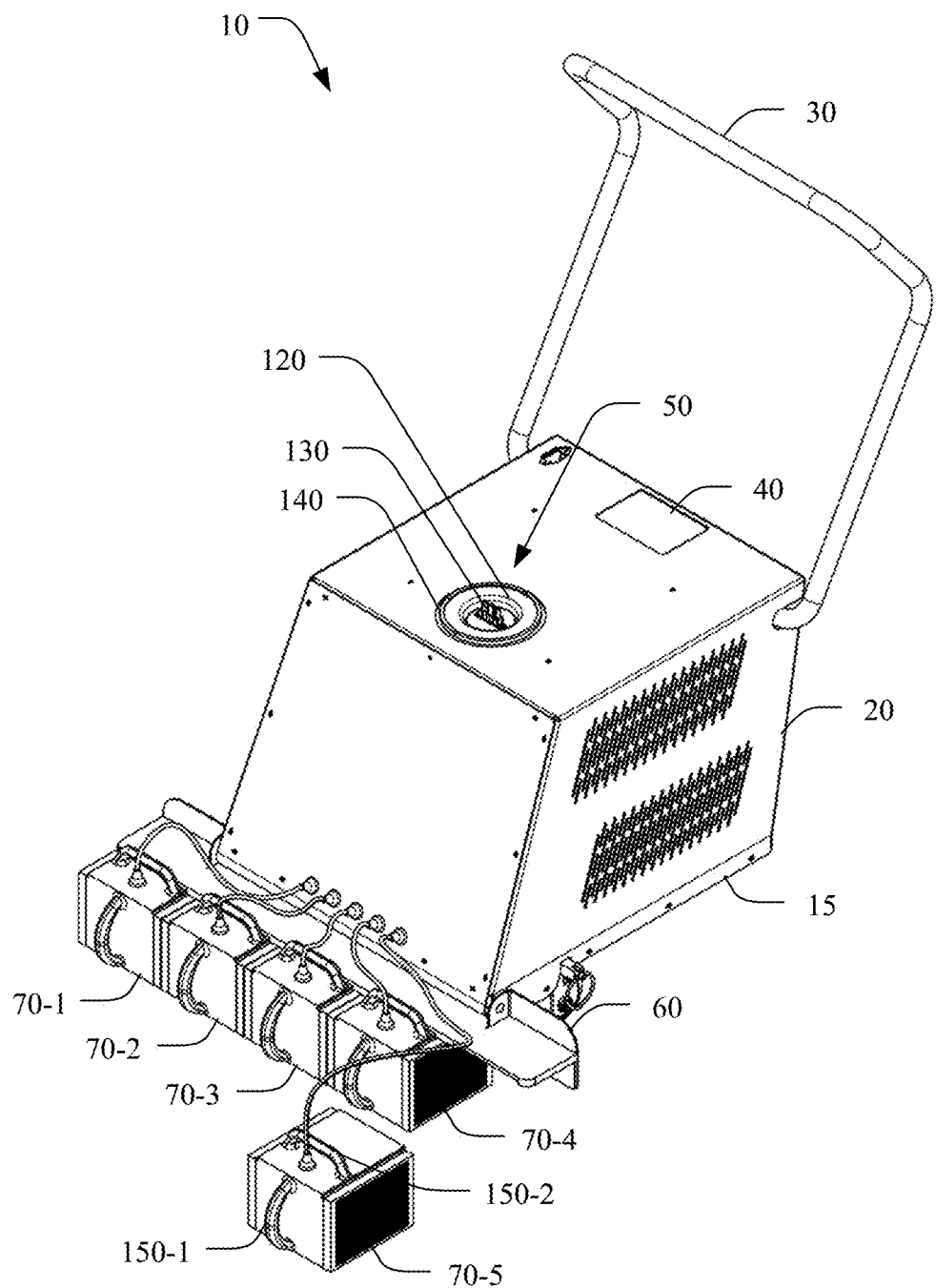
FIG. 3 is a right-side isometric view of the MUFC device of FIG. 1 with an extending radiation unit, according to an embodiment of the present disclosure.

In one embodiment, one or more of the radiation units 70 may be configured for being pulled-out of the UV panel 60 to be used as a handheld unit to cure or disinfect elevated surfaces or those at a significant height from the ground including constrict spaces or surfaces inside or outside objects such as cabinets. For example, the radiation units 70 may be wirelessly or physically coupled using cables such as cables (FIG. 3) to the control system. In case of a physical connection, heights up to which surfaces may be treated by the radiation units 70 may depend on lengths of cables connected thereto. In one example, the cable lengths may allow the radiation units 70 to extend up to a height of approximately 6 feet from the ground for treating surfaces from a distance of approximately one foot or less. The cables may be stored on one or more retractable reels (not shown) disposed on the chassis 90 and may be connected to the control system, i.e., the power supply unit 110 and the control device 100. In some embodiments, the retractable reels may be stowed on or integrated to the UV panel 60. The retractable reels may be configured to maintain a predetermined tension in the cables attached to the radiation units 70.

The cables may supply power and control signals to the radiation units 70. However, in some embodiments, each of the cables may be implemented as a compendium cable including an airflow tube (not shown) in addition to the cables being attached to the control system. The airflow tube may supply an airstream from an airflow source (not shown) of any predetermined type for cooling a respective radiation unit. For example, a suction airstream may be applied using a vacuum module (not shown) via the airflow tube, which may create a negative pressure within a radiation unit to draw out the hot air around a radiation source within that radiation unit such as the radiation unit 70-1. Additionally, or alternatively, each of the radiation units 70 may be fitted with a blower module such as a fan to augment the cooling of that radiation unit. Other embodiments may include one or more air openings (not shown) in the radiation units 70 for allowing the air driven by the airflow source attached to MUFC device 10 to pass through these air openings for cooling the radiation units 70. In some other embodiments, the radiation units 70, and therefore the radiation sources therein, may be water-cooled. Further, the one or more retractable reels attached to the cables may be driven manually by an operator or automatically by the control device 100 in response to a user input. Further, each of the radiation units 70 may include one or more handles such as handles 150-1 and 150-2 (collectively, handles 150) to assist in maneuvering such radiation units 70 in and out of the UV panel 60.

In one embodiment, the MUFC device 10 may be configured to transition from a floor configuration to a non-floor configuration, and vice versa. In the floor configuration (FIGS. 1-3), the UV panel 60 including the radiation units 70 may be configured to project the UV light towards the ground substantially underneath the UV panel 60. For example, in a rest position, the UV panel 60 may be adapted to orient a bottom-side, which may also be a radiation-emitting side, of at least one of the radiation units 70 substantially parallel to the ground. The radiation-emitting side may refer to any side, end, portion, section, location, direction, window or opening, position, or any other aspects of a radiation unit such as the radiation unit 70-1 through which the generated UV light may be projected exterior to that radiation unit. In another example, the radiation-emitting sides of the radiation units 70 may be oriented substantially parallel to the ground while being at a predetermined angle or orientation with respect to the UV panel 60. In yet another example, the radiation-emitting sides of the radiation units 70 may be substantially parallel to the ground while being non-parallel to the mobile carriage 15.

Figure 4:
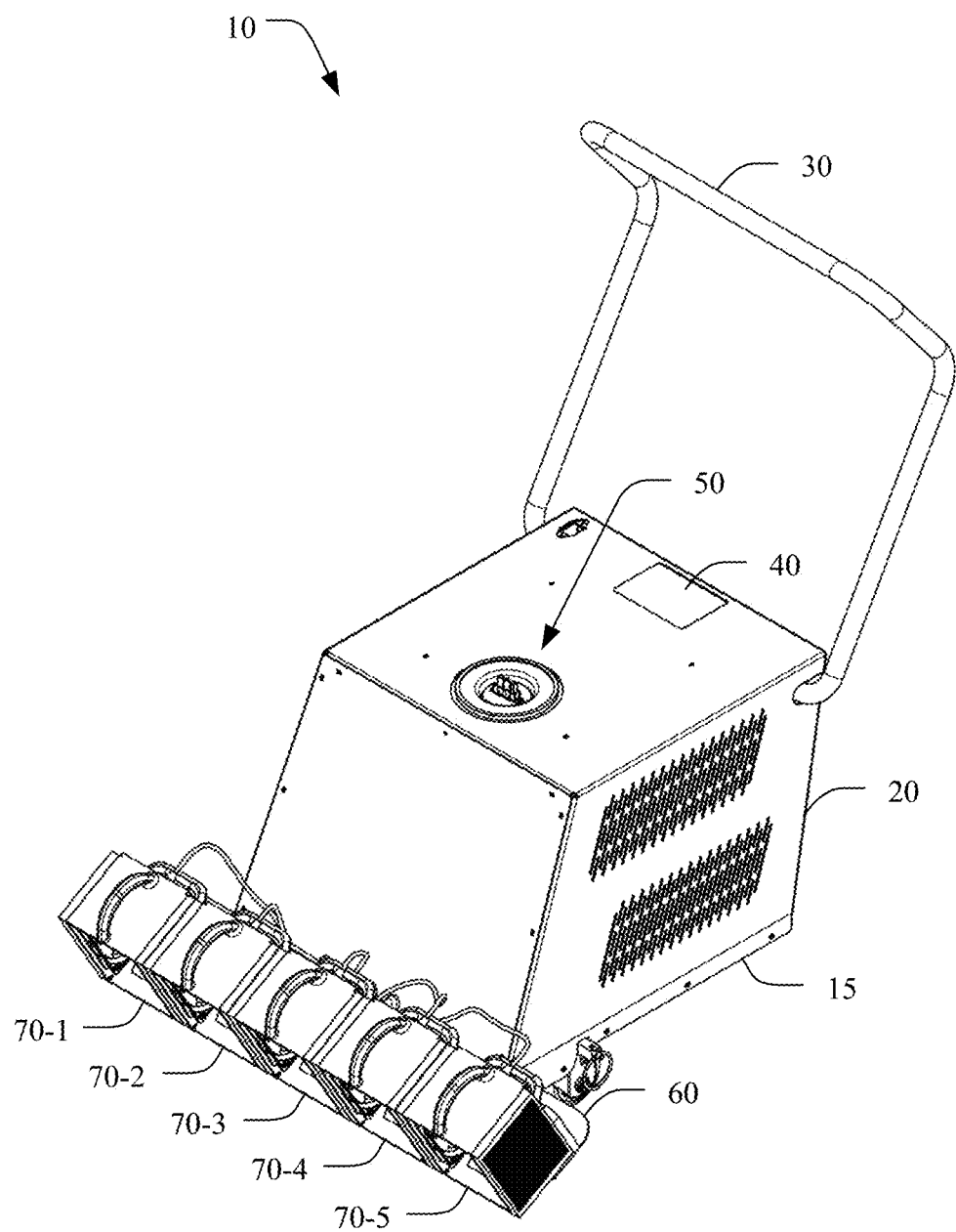
FIG. 4 is a right-side isometric view of the MUFC device of FIG. 1 in a non-floor configuration, according to an embodiment of the present disclosure.

In the non-floor configuration (FIG. 4), the UV panel 60 may be configured to move about a horizontal axis so that the radiation-emitting side of at least one of the radiation units 70 orients away from the ground underneath the UV panel 60. One having ordinary skill in the art may contemplate any suitable movements including, but not limited to, pivot rotary, pan, swivel, tilt, extend, and slide for moving the UV panel 60 based on the design thereof. In a tilted position, the UV panel 60 may be adapted to pivot in different orientations along a circumference of an imaginary circle having the horizontal axis passing through its center. In one example, as illustrated, the UV panel 60 may be adapted to pivot outwards from the rest position for driving the radiation-emitting sides of the radiation units 70 at angles up to approximately 100 degrees with the horizontal axis, thereby projecting the UV light away from the mobile carriage 15. In another example (not shown), the UV panel 60 may be adapted to pivot inwards from the rest position for driving the radiation-emitting side of the radiation units 70 at angles up to approximately 10 degrees with the horizontal axis, thereby projecting the UV light towards the ground underneath the mobile carriage 15.

Figure 5:
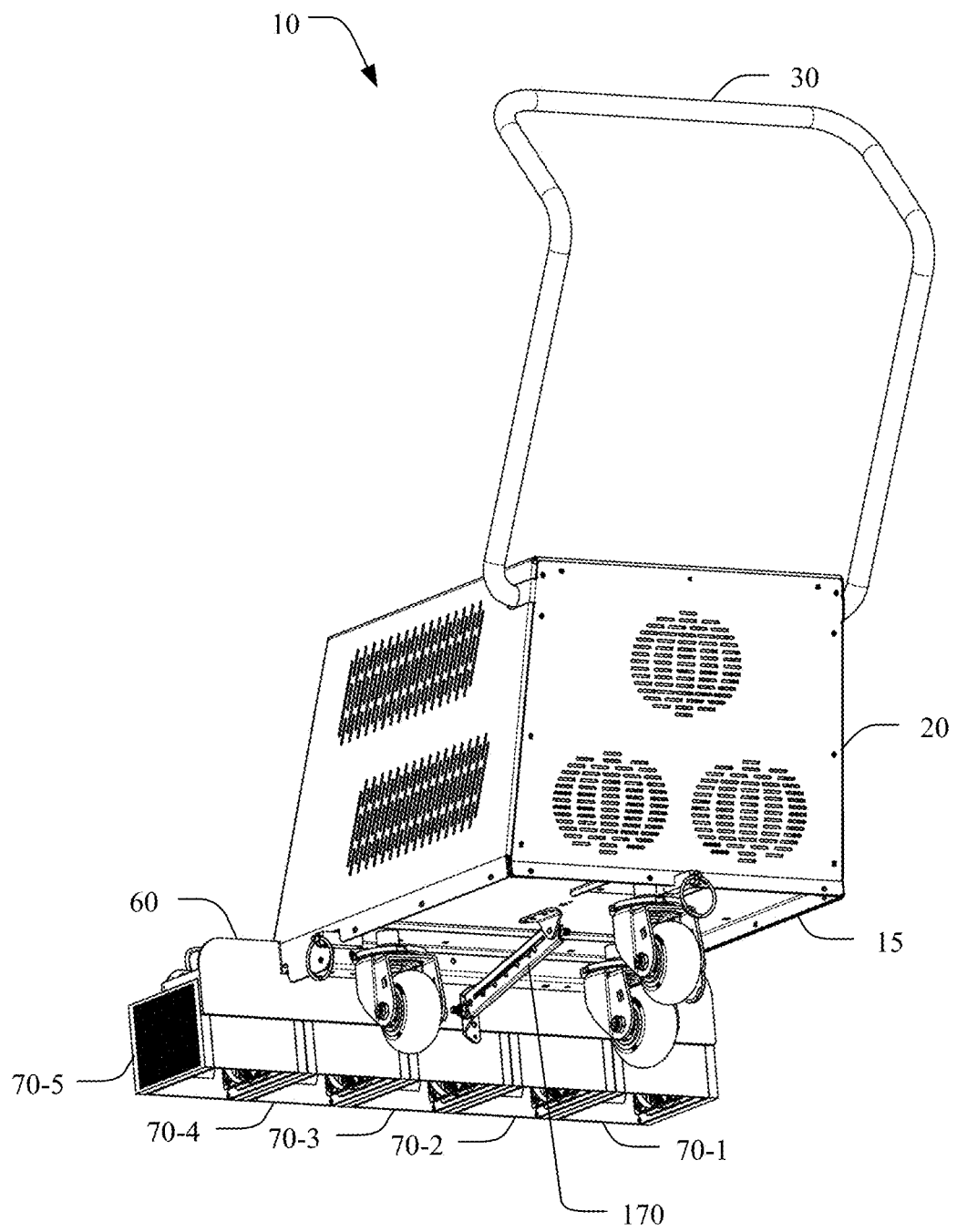
FIG. 5 is a rear perspective view of the MUFC device of FIG. 1 illustrating the bottom side thereof, according to an embodiment of the present disclosure.
Figure 6:
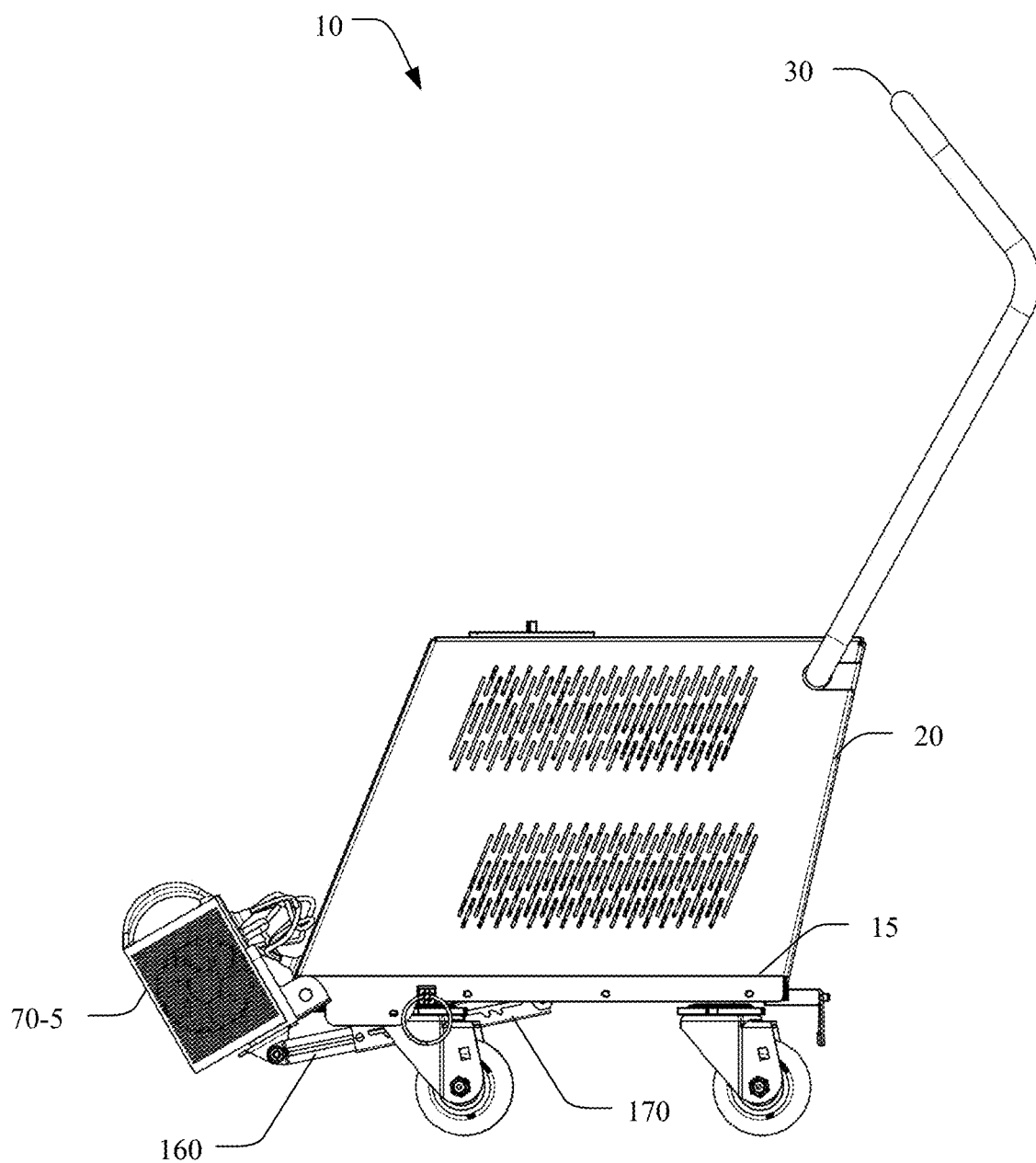
FIG. 6 is a right-side elevation view of the MUFC device of FIG. 4, according to an embodiment of the present disclosure.

With respect to the above configurations of the MUFC device 10, the UV panel 60 may be adapted to transition between the rest position and the tilted positions using a variety of mechanisms known in the art, related art, or developed later. In one embodiment (FIGS. 5-6), the UV panel 60 may be coupled to a ratchet 160 that may reciprocate linearly within a rail frame 170 to drive the UV panel 60. The ratchet 160 may be coupled to the UV panel 60 in a partly extended configuration, hereinafter referred to as zero-point position, while keeping the UV panel 60 at the rest position. The ratchet 160 may be driven to linearly extend out of the rail frame 170 for pivoting the UV panel 60 outwards from the zero-point position into a first tilted position. Similarly, the ratchet 160 may be moved backwards into the rail frame 170 from the zero-point position to pivot the UV panel 60 inwards into a second tilted position. The ratchet 160 may be driven via any suitable mechanical linkages such as gears and motors controlled by the control device 100.

Figure 7:
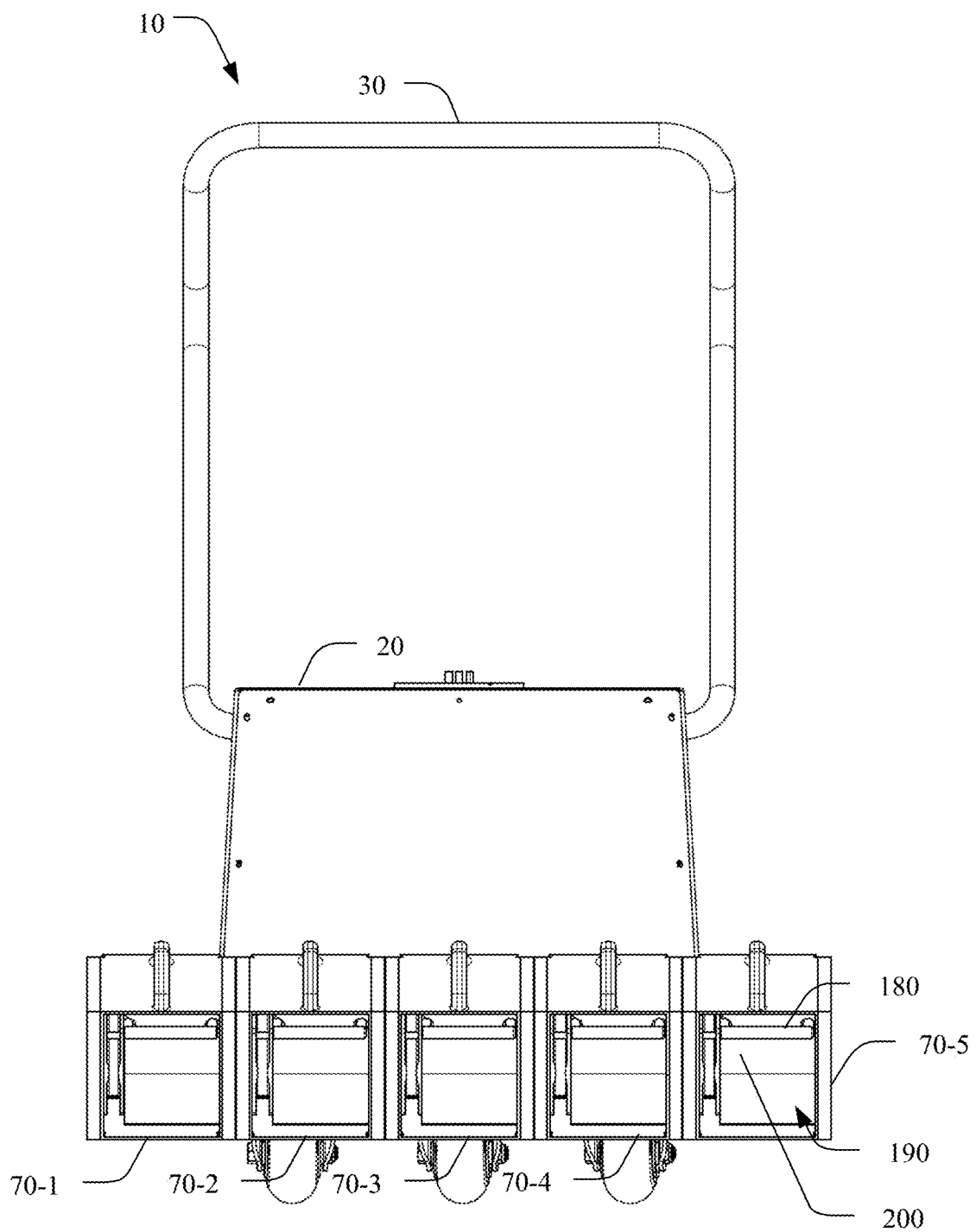
FIG. 7 is a front elevation view of the MUFC device of FIG. 4, according to an embodiment of the present disclosure.

In the tilted position of the UV panel 60 (FIG. 7), one or more of the radiation units 70 may be configured to project the UV light at surfaces up to a height of approximately one foot from the ground and towards the front of the MUFC device 10. In one embodiment, each of the radiation units 70 may include a radiation source 180 such as a UV lamp enclosed in a protective body having a radiation window 190, which may be adapted as an opening or a radiation filter such as optical filters, thereby defining the radiation-emitting side. The radiation source 180 may be placed behind the radiation window so that a predetermined radiation emitted by the radiation source 180 is projected through the radiation window 190 on to a target surface. The radiation window 190 of each of the radiation units 70 may face towards the floor upon being received with the UV panel 60 in the rest position.

The radiation source 180 such as the UV lamp may be a pulsed radiation source, a continuous radiation source, or a set of both the pulsed radiation and the continuous radiation sources. The pulsed radiation source may be configured by the control device 100 to emit pulses of UV light of a predetermined energy intensity within a predefined or dynamically defined wavelength range. In some embodiments, the pulsed radiation source may be configured by the control device 100 to have a pulse frequency and/or pulse duration that may cause the emitted pulsed UV light to appear as continuous to a human eye. On the other hand, the continuous radiation source may be configured by the control device 100 to emit a continuous stream of UV light. In some embodiments, the continuous radiation source may be turned on and off at a predetermined frequency by the control device 100 to emit pulses of UV radiation. The radiation source 180 may be designed as a bulb, a light emitting diode (LED), a lamp, or any other types known in the art, related art, or developed later, or any combination thereof. In one example, the radiation source 180 may be a strip of one or more UV LEDs configured to emit pulses of UV light. Other examples may include UV bulbs, which may be configured for pulsed or near continuous emission of the UV light. In some embodiments, the radiation source 180 may be flexible. In some other embodiments, a radiation unit such as the radiation unit 70-5 may include a flexible radiation source configured to acquire a larger geometry when extended or pulled-out of UV panel 60.

In one embodiment, each of the radiation units 70 may include one or more adjustable reflectors such as an adjustable reflector 200 around the respective radiation sources such as the radiation source 180 to converge or diverge the emitted UV light on to a target surface, or a radiation-curable coating thereon, through the radiation window 190 of that radiation unit such as the radiation unit 70-5. In one embodiment, the adjustable reflectors such as reflector 200 may be configured by the control device 100 to change their geometry or positions based on positions of (1) the respective radiation units 70 or (2) the UV panel 60. For example, the reflector 200 may have a curved geometry that may be adjusted by the control device 100 via mechanical linkages (not shown) for the reflector to have a relatively low curvature when the UV panel 60 is in the tilted position vis-à-vis the reflector curvature when the UV panel 60 is in the rest position. As a result, the reflector 200 upon having a lower curvature may increase the relative UV intensity received by a surface by focusing the UV light to a narrow surface area. In another embodiment, the control device 100 may be configured to adjust the intensity of the projected UV light depending on the position of the reflector 200 with respect to the horizontal axis or the vertical axis. For example, the control device 100 may be configured to drive the radiation sources such as the radiation source 180 to increase the intensity of the project UV light according to an increase in the tilt angle of the reflectors with respect to the horizontal axis from the rest position of the UV panel 60. Farther the radiation-emitting sides of the radiation units 70 from the ground, greater may be the UV intensity. Further, the reflector 200 may be suitably positioned with respect to the radiation source 180 such as behind or front of the radiation source 180 to direct a maximum amount of UV light towards the ground, a target surface, or a desired direction.

Figure 8:
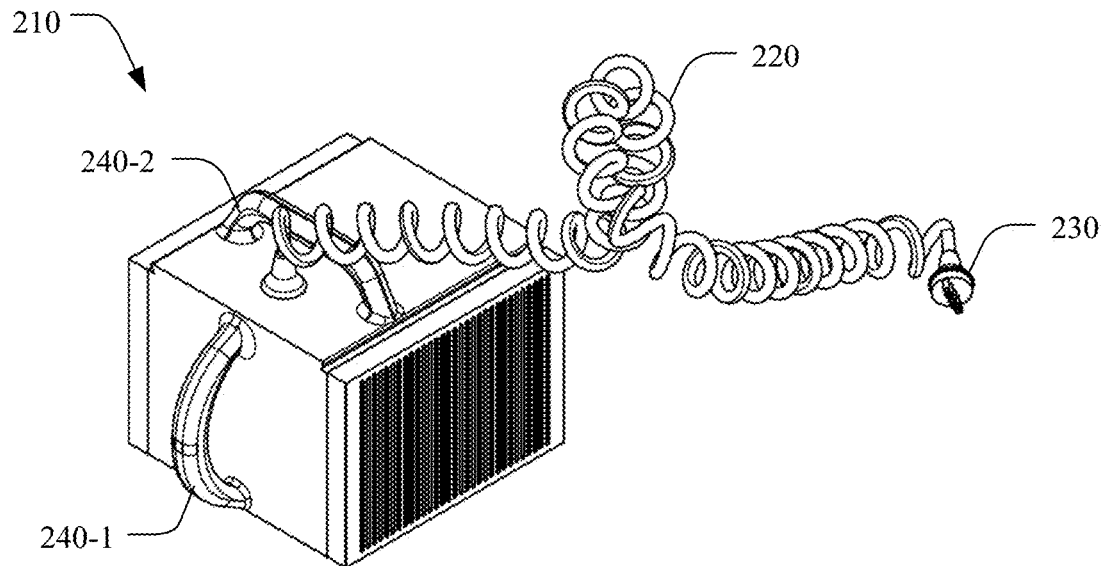
FIG. 8 is an isometric view of an exemplary independent radiation unit configured for use with the MUFC device of FIG. 1, according to an embodiment of the present disclosure.
Figure 9:
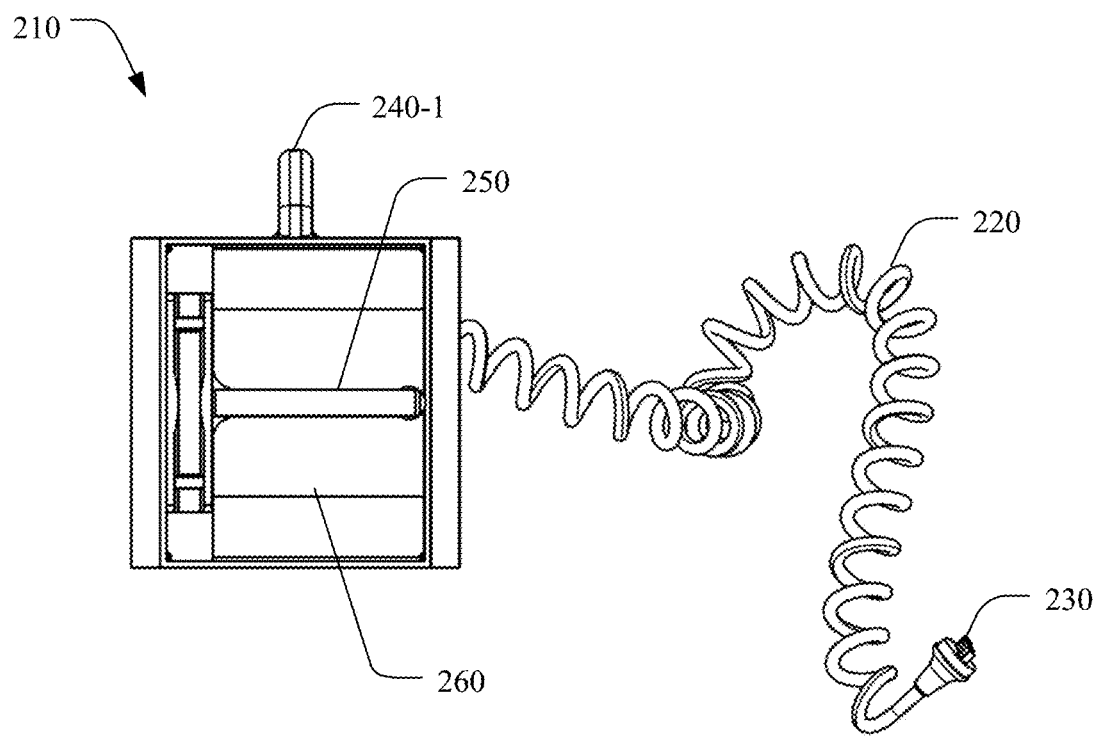
FIG. 9 is a bottom elevation view of the radiation unit of FIG. 8, according to an embodiment of the present disclosure.

In addition to the radiation units 70 coupled to UV panel 60, the MUFC device 10 may be coupled to additional standalone devices via the power connector 50 for extended functionalities. In a first implementation (FIGS. 8-10), an independent handheld radiation unit 210 may be connected to the power connector 50. The handheld radiation unit 210 may include a power cable 220 such as a coiled power cable 220 having any suitable length to assist in accessing surfaces at a significant height such as 8 feet to 10 feet from the ground depending on the length of the power cable 220. The power cable 220 may include a plug 230 compatible with the power connector 50 for being connected thereto. In some embodiments, the handheld radiation unit 210 may operate in communication with the control device 100 for a tandem operation. The handheld radiation unit 210 may include handles 240-1, 240-2 (collectively, handles 240) for easy maneuverability and a radiation source 250 such as a UV lamp.

Figure 10:
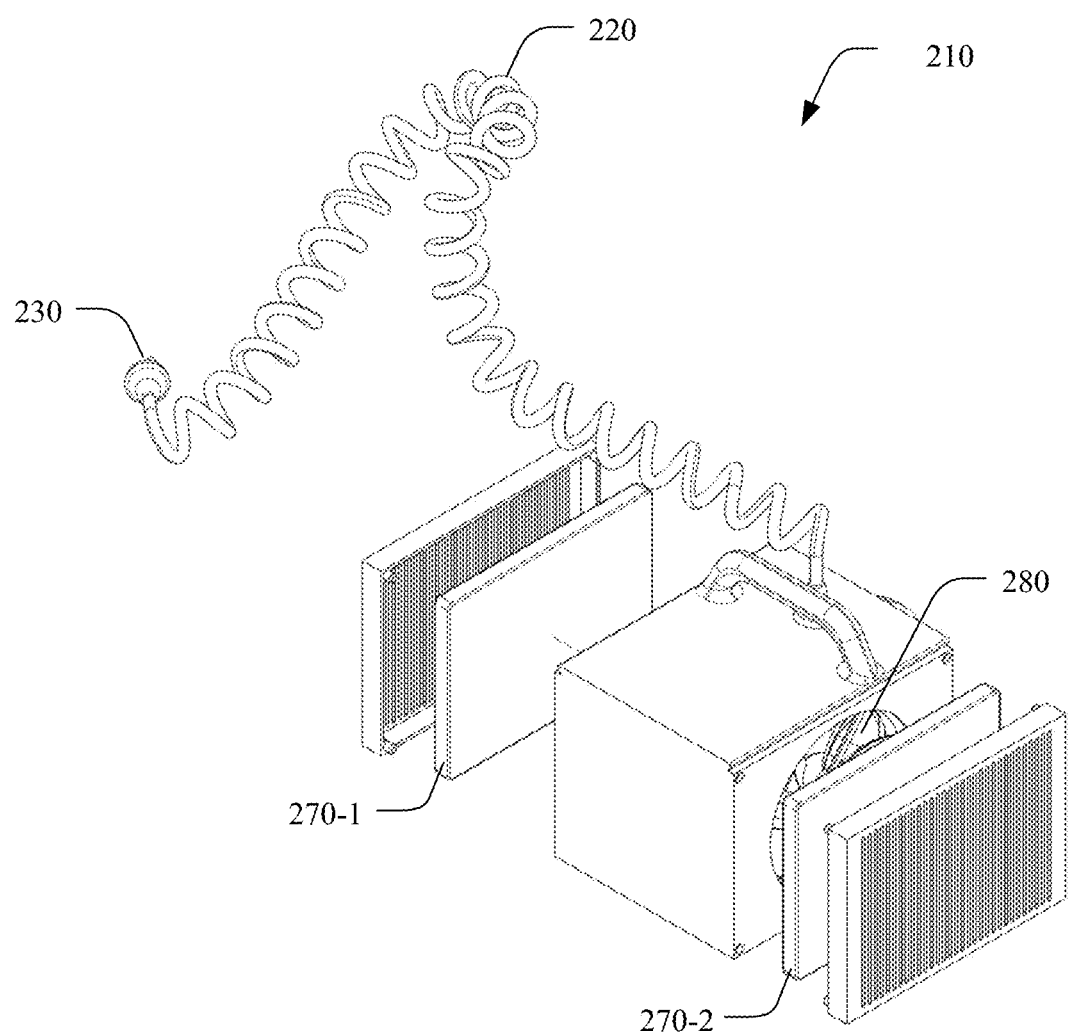
FIG. 10 is an exploded view of the radiation unit of FIG. 8, according to an embodiment of the present disclosure.

In one embodiment, the handheld radiation unit 210 may also include one or more controllable reflectors 260, similar to the adjustable reflector 200, which may be configured by the control device 100 to change their geometry or positions based on their angle with respect to the horizontal axis during use. Such an angle may be measured using any of a variety of components or mechanisms known in the art, related art, or developed later including, but not limited to, a gyroscope, an accelerometer, an inclinometer, and so on in combination with an on-device control unit (not shown). The control device 100 may communicate with the on-device control unit and adjust the intensity of the UV light generated by the radiation source 250 either directly or by adjusting the geometry or position of the controllable reflectors 260. As illustrated in FIG. 10, similar to the radiation units 70, the handheld radiation unit 210 may include filters 270-1, 270-2 (collectively, filters 270) and a cooling unit such as a fan 280. Examples of the filter may include, but not limited to, a high efficiency particulate air (HEPA) filter, an ultra-low penetration air (ULPA) filter, a Micro Fresh filter, an allergen filter, and a carbon-activated filter, or any combination thereof.

Figure 11:
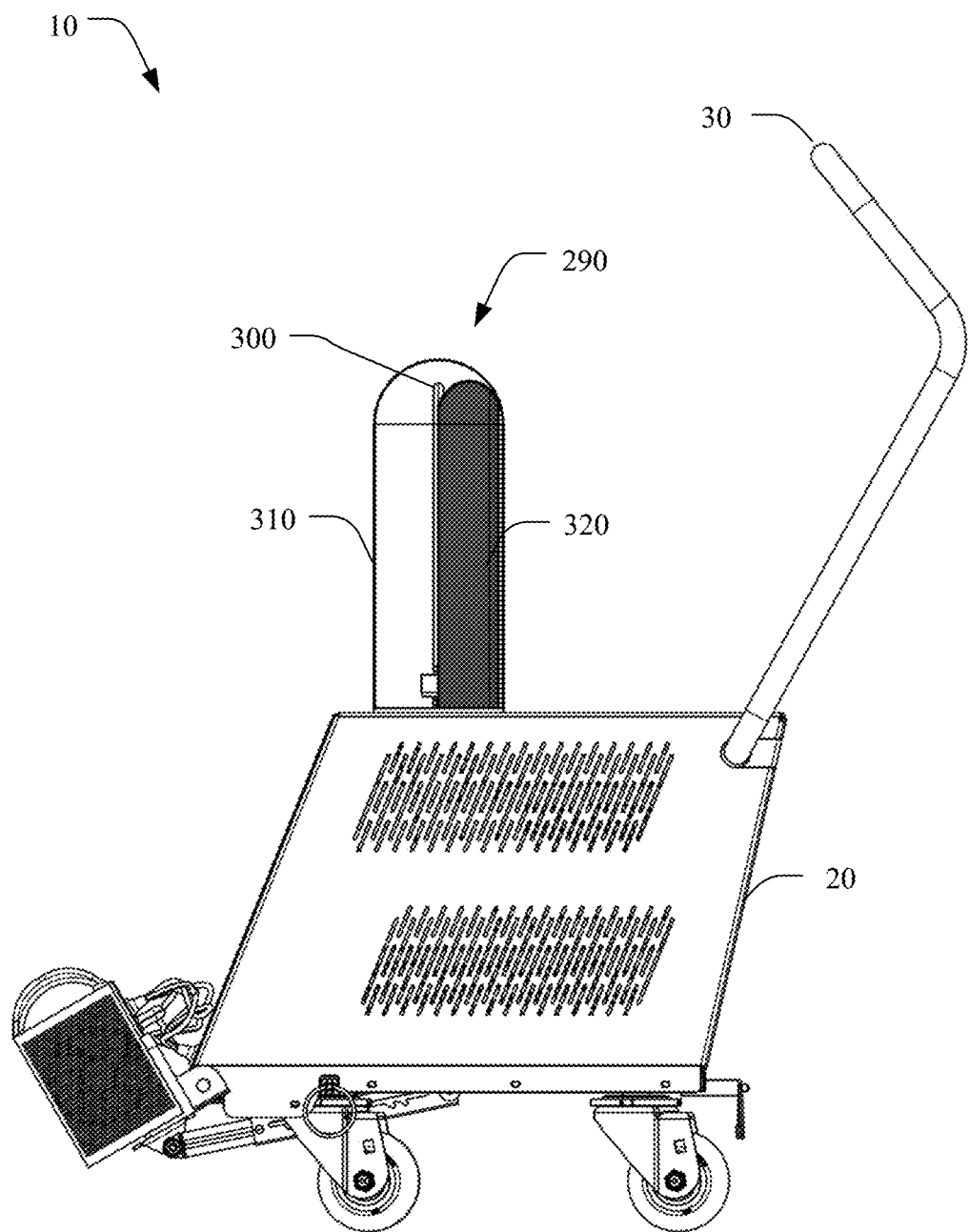
FIG. 11 is a right-side elevation view of the MUFC device of FIG. 4 including an exemplary UV tower fitted with a rotatable reflector, according to an embodiment of the present disclosure.
Figure 14:
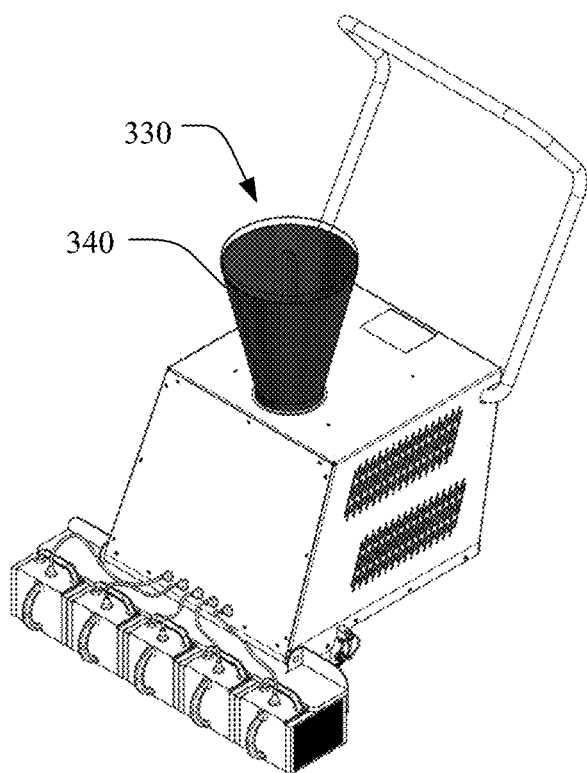
FIG. 14 is a right-side isometric view of the MUFC device of FIG. 1 including an exemplary ceiling UV projector, according to an embodiment of the present disclosure.
Figure 15:
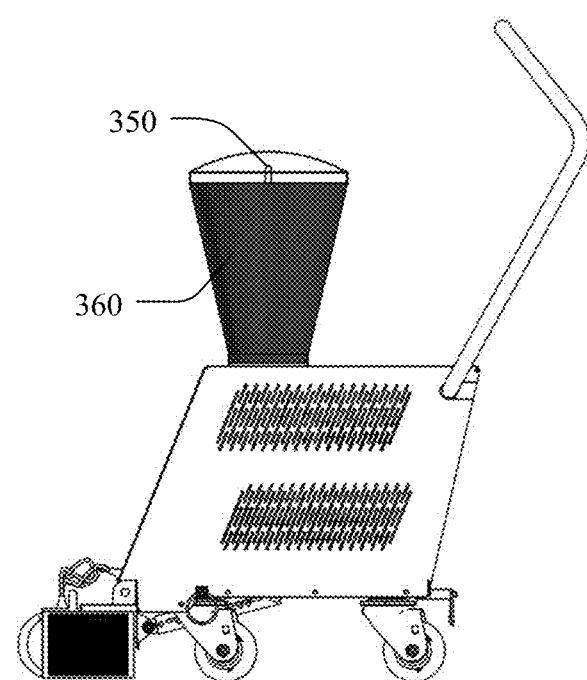
FIG. 15 is a right-side elevation view of the MUFC device of FIG. 14, according to an embodiment of the present disclosure.

In a second implementation (FIGS. 11-13), a UV tower 290 may be connected to the power connector 50 for transforming the MUFC device 10 into an area UV disinfection device in addition to a curing device. The UV tower 290 may include a transparent housing 300 enclosing a radiation source 310 such as a UV lamp configured to project the UV light exterior to the UV tower 290. The housing 300 may be made of any suitable materials known in the art, related art, or developed later including quartz that limits attenuation of the UV light passing therethrough. The housing 300 may have a shape, size, and cross-section compatible for being mounted on the power connector 50. For example, the housing 300 may be cylindrical having a circular cross-section for being secured in the recess 140 associated with the power connector 50 using any suitable mechanisms known in the art, related art, or developed later including a snap fit. In one embodiment, the UV tower 290 may also include a rotatable reflector 320 located within the housing 300 and configured to rotate about the UV lamp 310 or a vertical axis for selectively projecting the UV light in an intended direction. The rotatable reflector 320 may be suitably positioned with respect to the UV lamp 310 such as behind or front of the UV lamp 310 to direct a maximum amount of UV light towards a target surface or a desired direction. The rotatable reflector 320 may be adapted to rest on the body 120 of the power connector 50 and configured to rotate based on rotation of the power connector body 120, as illustrated in FIGS. 12-13.

In another embodiment, the UV tower 290 may include an on-board control unit (not shown) and a power unit (not shown) to drive the rotatable reflector 320. In yet another embodiment, the rotatable reflector 320 may include multiple reflecting sections (not shown), each capable of rotating in different directions in tandem with each other. In still another embodiment, each of the rotatable reflecting sections may rotate or operate independent of each other. In some embodiments, the rotatable reflector 320 or the rotatable reflecting sections may gradually rotate at fixed or gradually changing angles such as 120 degrees, 135 degrees, 180 degrees, 240 degrees, and 360 degrees, or any other suitable angles, with respect to the radiation source for intended surface coverage. Similar to the radiation units 70, geometries of the rotatable reflector 320 as well as the reflecting sections may be increased or decreased via any suitable mechanical linkages known in the art such as those discussed above. In one embodiment, the control device 100 may adjust the intensity of the generated UV light based on (1) predetermined rotational speeds or positions of the rotatable reflector 320 or the reflecting sections with respect to the UV panel 60, radiation units 70 connected thereto, or a target surface, (2) operational modes of the MUFC device 10, or (3) a user input to increase or decrease the projected intensity of the UV light. Such rotational speeds may be predefined or dynamically defined based on (i) various aspects of a target surface and (ii) duration and extent of UV exposure as well as a number of times such exposure may be required. Examples of these aspects may include, but not limited to, physical aspects (e.g. physical states, temperature, pressure, weight or mass, volume, velocity, concentration, electric charge, viscosity, etc.), chemical aspects (e.g., enthalpy, toxicity, pH value, reactivity, flammability, etc.), and biological aspects (e.g., living organisms, plants or plant products, organic residues, etc.), or any combination thereof. The control device 100 may also drive the UV tower 290 to generate pulses of UV light instead of a continuous stream, for example, during a disinfection mode for disinfecting a target surface. The UV tower 290 may also include filters (not shown) and cooling mechanisms (not shown) such as those mentioned above.

In a third implementation, a ceiling UV projector 330 may be connected to the power connector 50 for providing a specific functionality of the area UV disinfection device in addition to curing. The ceiling UV projector 330 may be configured to project the UV light upwards at a high intensity. In one embodiment, the ceiling UV projector 330 may include an inverted-cone housing 340 enclosing a radiation source 350 such as a UV lamp. The top of housing 340 may be transparent for allowing the UV light to pass through and lateral edges may be substantially covered by an inverted-cone reflector 360 for projecting the UV light in the upward direction. The length of the lateral edges and dimensions of the circular cross-sections may be selected based on the intended coverage of a target surface and the UV intensity received per surface area.

In one embodiment, the inverted-cone reflector 360 may have an adjustable geometry and the ceiling UV projector 330 may further include an on-board control unit (not shown) in communication with the control device 100. The adjustable inverted-cone reflector 360 may be made of two or more curved reflector panels capable of overlapping with each other via known mechanical linkages (not shown) to decrease the geometry of the inverted-cone reflector 360. One having ordinary skill in the art may also contemplate to increase the geometry of the inverted-cone reflector 360 relative to the space available within the inverted-cone housing 340. In said embodiment, the control device 100 may be configured to adjust the UV intensity based on the geometry of the inverted-cone reflector 360. For example, the control device 100 in communication with the control unit may increase the UV intensity when the geometry of the inverted-cone reflector 360 is decreased. In another example, the control device 100 in communication with the control unit may increase the UV intensity when the geometry of the inverted-cone reflector 360 is increased. The ceiling UV projector 330 may also include filters (not shown) and cooling mechanisms (not shown) such as those mentioned above. In some embodiments, the ceiling UV projector 330 may not include the inverted-cone housing 340. In some other embodiments, the ceiling UV projector 330 may be integrated with the UV tower 290. In some embodiments, the ceiling UV projector 330 may be configured to swivel or tilt about a horizontal axis upon being triggered by the control device 100 to project the UV light on surfaces proximate to the ceiling perpendicularly above the MUFC device 10.

The MUFC device 10 may be implemented to cure or disinfect target surfaces through a set of integrated UV devices and externally connected accessories. In one embodiment, the MUFC device 10 may be configured to operate in a curing mode and a disinfection mode, each of which may be implemented in any order. During operation, an operator may select one of the modes such as the curing mode and the disinfection mode using any of the input devices known in the art, related art, or developed later connected to the MUFC device 10. For example, the operator may login on an interactive display screen of the display unit 40 in communication with the control device 100 and select one of those modes on the screen.

Curing Mode

When the curing mode is selected, the control device 100 may allow the UV panel 60 to transition between the rest position and the tilted position, and vice versa for curing radiation-curable coatings on surfaces on the ground and surfaces proximate thereto including those elevated up to approximately one foot from the ground, e.g., baseboards, trims, etc. In some embodiments, the control device 100 may be configured to automate and repeat such transitions of the UV panel 60 during the curing mode. In one embodiment, the control device 100 may adjust the intensity of the project UV light depending on the position of reflector such as the reflector 200 in the radiation units 70 with respect to the horizontal axis. For example, the control device 100 may increase the UV intensity as a tilt angle of the reflector such as the reflector 200 changes from a predetermined base angle such as zero degree with respect to the horizontal axis at the rest position of the UV panel 60.

In another instance, the control device 100 may keep the radiation units 70 unlocked in the UV panel 60. In order to cure surfaces at a significant height from the ground, an operator may pull-out one or more radiation units 70 from the UV panel 60 and use them as handheld UV units. The height up to which a surface may be accessed for curing by the radiation units 70 may depend on the lengths of cables through which the radiation units 70 may be connected to the MUFC device 10. In one example, the radiation units 70 may have cable lengths sufficient to cure surfaces up to heights of approximately 6 feet from the ground. In another example, the radiation units 70 may be wirelessly coupled to the control system or additionally have an on-board battery for use at heights greater than approximately 6 feet.

Additionally, or alternatively, the operator may connect standalone accessories connected to the power connector 50 for curing radiation-curable coatings. In a first implementation, a standalone handheld UV unit 210 including one or more controllable reflectors 260 may be connected to the power connector 50 via the cable 220, which may have a length enough to provide access to surfaces at least up to approximately 10 feet from the ground for curing radiation-curable coatings thereon. In one embodiment, the control device 100 may drive the handheld UV unit 210 to project the UV light on target surfaces. Depending on the angle of controllable reflectors 260 with respect to the horizontal axis during use, the control device 100 may drive the handheld UV unit 210 to project the UV light of higher intensity. Alternatively, the control device 100 may adjust the geometries or positions of the reflectors 260 within the handheld UV unit 210 to focus the projected UV light to deliver a high UV dose to the target surface.

In a second implementation, the UV tower 290 including the rotatable reflector 320 may be connected to the power connector 50 by the operator. The UV tower 290 may be driven to project the UV light on target surfaces at heights of approximately one foot or more from the ground depending on the height of the UV tower 290. During the curing mode, the control device 100 may limit the rotation of the rotatable reflectors such as the rotatable reflector 320 to direct the UV light only to the front of the mobile carriage 15, e.g., at fixed or gradually changing angles up to 180 degrees, with respect to the mobile carriage 15 or the horizontal axis. Further, the control device 100 may adjust the intensity of the generated UV light based on rotational speeds or positions of the rotatable reflector 320 with respect to the UV panel 60, the radiation units 70 connected thereto, or a user input. For example, the control device 100 may be configured to increase the UV intensity when a reflecting side of rotatable reflector 320 is not parallel to the UV panel 60.

In a third implementation, an operator may connect the ceiling UV projector 330 to the power connector 50 for curing radiation-curable coatings on the ceiling or surfaces proximate thereto. The control device 100 may drive the ceiling UV projector 330 via the power connector 50 to project the UV light towards the ceiling above the MUFC device 10. The ceiling UV projector 330 may be driven to generate the UV light at a high intensity sufficient to cure a radiation-curable coating on the ceiling above the MUFC device 10, or surfaces proximate thereto, within 10 minutes or less from a distance of approximately 6 feet or less from the ground. In some embodiments, the control device 100 may activate the ceiling UV projector 330 to swivel or tilt about a horizontal axis to project the UV light on to surfaces proximate to the ceiling, which may be perpendicularly above the MUFC device 10, for example, at a height of approximately 9 feet from the ground. In some embodiments, the ceiling UV projector 330 may be integrated with the UV tower 290.

Disinfection Mode

When room or large area UV disinfection is desired, the operator may deactivate the curing mode and remotely select the disinfection mode on the MUFC device 10. The operator may devoid human occupancy in the designated area where the disinfection is to be performed prior to activating the disinfection mode to avoid health hazards due to the UV light.

When the disinfection mode is activated, the control device 100 may secure the received radiation units 70 in the UV panel 60 using any of the securing mechanisms known in the art such as mechanical locks and electromagnetic locks depending on the materials from which the radiation units 70 and the UV panel 60 are made. Once secured, the radiation units 70 may not be removable from the UV panel 60 unless the disinfection mode is changed, the MUFC device 10 is turned off, or any similar accessory such as the UV tower 290 capable of providing area UV disinfection is disabled or not connected to the MUFC device 10. In some embodiments, the secured radiation units 70 may become detachable when the power supplied to the radiation units 70 may be cut-off. Further, the control device 100 may drive the MUFC device 10 to move autonomously within a designated space and activate the UV panel 60 as well as any standalone accessory connected to the power connector 50 simultaneously. For example, the control device 100 may drive the UV panel 60 to continuously transition between the rest position and the tilt position while projecting the pulses of UV light at surfaces up to approximately one foot from the ground. Additionally, the UV tower 290 alone or in combination with the ceiling UV projector 330 may be activated to project the pulses of UV light on target surfaces at heights up approximately 10 feet from the ground. Further, the control device 100 may drive the rotatable reflector 320 to have a full 360-degree rotation within the UV tower 290. Alternatively, the control device 100 may drive a separate MUFC device 10 connected to the power connector 50 for operating two MUFC devices in tandem with each other for surface disinfection, or for curing.

The disinfection mode may be activated for a predefined or dynamically defined duration and may be interrupted either on-demand by the operator or based on preset or dynamically set conditions such as those indicated by various sensors (e.g., motion/vibration sensors, occupancy/proximity sensors, ozone sensors, temperature sensors, smoke sensors, pathogen level detection sensors, etc.) in communication with the MUFC device 10. Examples of these conditions may include, but not limited to, motion detection in the proximity of the MUFC device 10 or by remote sensors communicating therewith, temperature of a radiation source such as a UV lamp above a predefined threshold, an accumulation of ozone above a predefined threshold, and so on. Further, the control device 100 may be configured to adjust the intensity, dose, frequency, wavelength, pulse duration, or any other aspects of the UV light.

While the foregoing written description of the present disclosure enables one of ordinary skill to make and use what is considered presently to be the best mode thereof, those of ordinary skill will understand and appreciate the existence of variations, combinations, and equivalents of the specific embodiment, method, and examples herein. The present disclosure should therefore not be limited by the above described embodiment, method, and examples, but by all embodiments and methods within the scope and spirit of the present disclosure.

The order in which the methods are described is not intended to be construed as a limitation, and any number of the described method steps can be combined or otherwise performed in any order to implement the methods, or an alternate method. Additionally, individual aspects may be deleted from the method without departing from the spirit and scope of the subject matter described herein. Furthermore, aspects of the methods can be implemented in any suitable hardware, software, firmware, or combination thereof, that exists in the related art or that is later developed.

Notably, the figures and examples below are not meant to limit the scope of the present disclosure to a single embodiment, but other embodiments are possible by way of interchange of some or all of the described or illustrated elements.

What is claimed is:

1. A method comprising:
providing a mobile device including a UV panel holding at least one handheld radiation unit;
activating, using a control device, the at least one handheld radiation unit to emit UV light;
pivoting, using the control device, the UV panel about a horizontal axis for orienting the at least one handheld radiation unit towards at least one of a surface underneath the UV panel and an elevated surface proximate to the surface; and
configuring the at least one handheld radiation unit for being drawn out of the UV panel for curing or disinfecting a target surface.

2. The method of claim 1, wherein the step of pivoting further comprises transitioning the UV panel between the surface and the elevated surface while the at least one handheld radiation unit is projecting the UV light.

3. The method of claim 1, wherein the surface includes a floor.

4. The method of claim 1, further comprising moving, using the control device, the mobile device autonomously while the UV panel is pivoting or the at least one handheld radiation unit is emitting the UV light.

5. The method of claim 1, wherein the step of pivoting further comprises moving the UV panel for the at least one handheld radiation unit to project the UV light towards a portion of another surface, wherein the portion is underneath the mobile device.

6. The method of claim 1, wherein the step of providing the mobile device further comprises selecting one of the predefined modes of operation using the control device for driving the at least one handheld radiation unit and the UV panel, the predefined modes of operation including a first mode and a second mode, wherein the at least one handheld radiation unit is locked into the UV panel in the first mode and unlocked for being drawn out of the UV panel in the second mode by the control device.

7. The method of claim 1, wherein the UV light is a pulsed UV light.

8. The method of claim 1, wherein the step of pivoting further comprises moving, using the control device, the UV panel relative to the mobile device.

9. The method of claim 1, wherein at least one of the mobile device and the at least one handheld radiation unit includes a light emitting diode (LED).

10. The method of claim 1, wherein the mobile device is operably coupled to at least one of a card reader, a barcode reader, and a biometric scanner.

11. The method of claim 1, wherein the mobile device is operably coupled to a camera.

12. The method of claim 6, wherein the step of selecting further comprises the control device receiving a communication from an input device for selecting one of the predefined modes of operation, wherein the input device includes at least one of a camera and a computing device.

13. The method of claim 1, wherein the at least one handheld radiation unit includes a reflector.

14. The method of claim 1, further comprising manipulating, using the control device, an intensity of the UV light based on a position of a reflector with respect to the horizontal axis, wherein the reflector is operably coupled to the mobile device.

15. The method of claim 1, further comprising manipulating, using the control device, a position of a reflector based on a respective position of at least one of the UV panel and the at least one handheld radiation unit.

16. The method of claim 1, further comprising interrupting, using the control device, a selected mode of operation based on at least one of (i) a motion being detected by a sensor in communication with the mobile device, (ii) a temperature of a light source in the at least one handheld radiation unit above a predefined threshold, and (iii) an accumulation of ozone above a preset threshold.

17. The method of claim 1, wherein the UV panel includes one of an opening and a channel to facilitate airflow therethrough for cooling the at least one handheld radiation unit.

18. The method of claim 1, wherein at least one of the UV panel and the at least one handheld radiation unit includes an airflow source.

19. The method of claim 1, further comprising controlling, using the control device, a power connector (i) for supplying power to an electrical accessory or (ii) for being rotated about a predetermined axis, wherein the power connector is operably coupled to the mobile device.

20. The method of claim 1, wherein the mobile device is operably coupled to a user interface controllable using at least one of motion, touch, and voice.

* * * * *